United States Patent [19]

Samson et al.

[11] Patent Number: 4,571,240
[45] Date of Patent: Feb. 18, 1986

[54] CATHETER HAVING ENCAPSULATED TIP MARKER

[75] Inventors: Wilfred J. Samson, Saratoga; Jeffrey S. Frisbie, San Jose, both of Calif.

[73] Assignee: Advanced Cardiovascular Systems, Inc., Mountain View, Calif.

[21] Appl. No.: 522,820

[22] Filed: Aug. 12, 1983

[51] Int. Cl.4 ............................................. A61M 25/00
[52] U.S. Cl. ...................................... 604/96; 604/280; 128/658
[58] Field of Search ................... 604/96, 97, 100, 103, 604/264, 270, 280, 282, 283; 128/656, 658, 207.14

[56] References Cited

U.S. PATENT DOCUMENTS 3,605,750  9/1971  Sheridan et al. ............... 604/280 X
4,265,848  5/1981  Rüsch ................................ 604/96 X

FOREIGN PATENT DOCUMENTS 0033659  8/1981  European Pat. Off. ............ 128/658
940777  7/1982  U.S.S.R. .............................. 128/658

Primary Examiner—Stephen C. Pellegrino
Attorney, Agent, or Firm—Flehr, Hohbach, Test, Albritton & Herbert

[57] ABSTRACT

A catheter comprising a first elongate flexible member having a cylindrical outer surface and having proximal and distal ends. A metallic band of radio opaque material is disposed on the outer surface of the elongate member in the vicinity of the distal end of the elongate member. A tubular member of a flexible material is carried by the distal end of the elongate member and encapsulates the metallic band to prevent its accidental dislodgment from the tip of the catheter.

7 Claims, 4 Drawing Figures

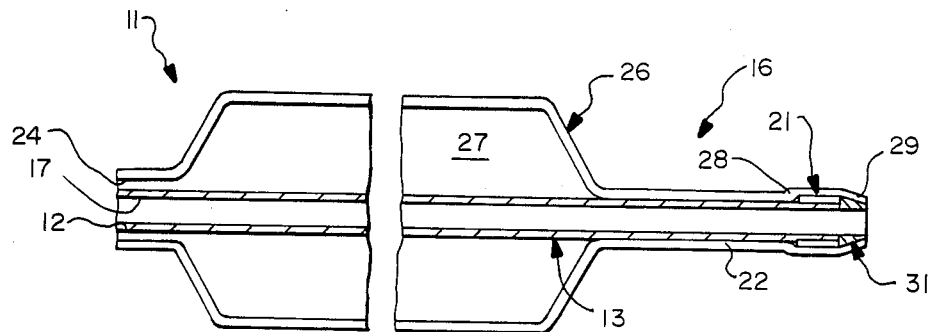
FIG.—1
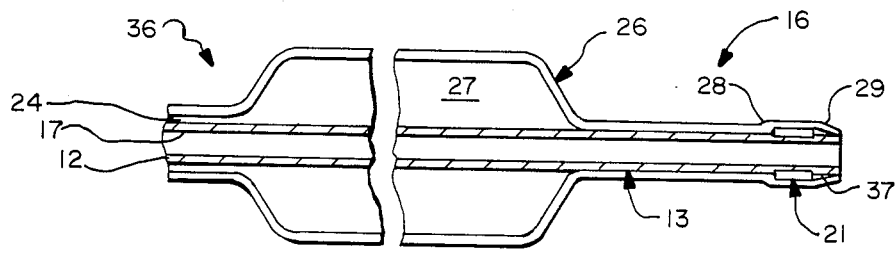
FIG.—2
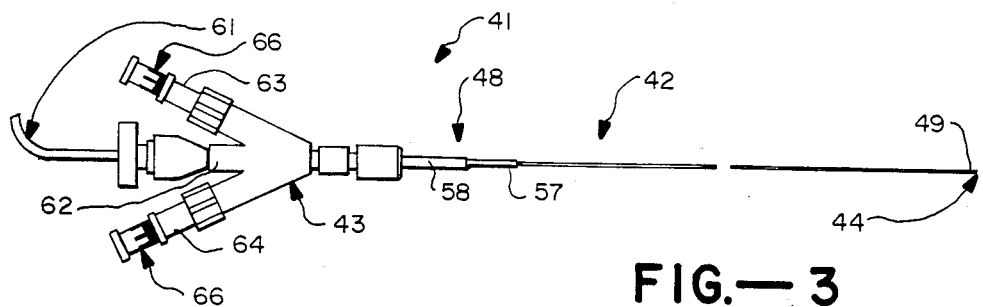
FIG.—3
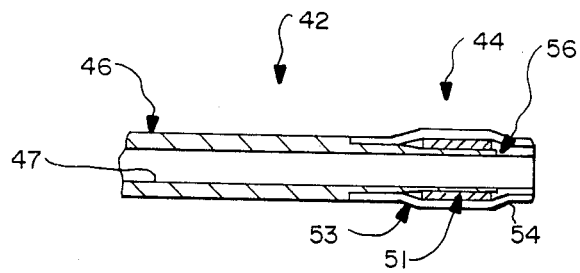
FIG.—4

CATHETER HAVING ENCAPSULATED TIP MARKER

This invention relates to catheters and more particularly to catheters of the type in which it is desired to mark the tips of the catheters with a radio opaque marker.

In percutaneous transluminal coronary angioplasty, catheters are often inserted into the cardiovascular system. In such operations, it is very often desirable to ascertain when the tip of the catheter has entered a lesion. Attempts have been made to place radio opaque markers at the tip of the catheter as, for example, by placing an epoxy on the end which is loaded with an radio opaque material which has been inadequate. Also a radio opaque band has been attached to the outer extremity. However, there has been the concern that the radio opaque band could fall off of the catheter tip and remain in the body of the patient which would have very undesirable consequences. Therefore there is a need for a new and improved catheter tip marker which overcomes these disadvantages.

In general, it is an object of the present invention to provide a catheter having a tip marker which is radio opaque and which cannot become accidentally dislodged.

Another object of the invention is to provide a catheter of the above character in which a tip marker has been encapsulated.

Another object of the invention is to provide a catheter of the above character which can be of very small size.

Additional objects and features of the invention will appear from the following description in which the preferred embodiments are set forth in detail in conjunction with the accompanying drawings.

FIG. 1 is a cross sectional view of a balloon catheter incorporating the present invention having an encapsulated tip marker at the distal end.

FIG. 2 is another embodiment of a balloon catheter of the type shown in FIG. 1 incorporating the present invention.

FIG. 3 is an elevational view of another catheter and in particular a reperfusion catheter incorporating the present invention and also having an encapsulated tip marker at the distal end.

FIG. 4 is a greatly enlarged cross sectional view of the distal end of the catheter shown in FIG. 3.

In general, the catheter of the present invention consists of a flexible member having a cylindrical outer surface and having proximal and distal ends. A metallic band of a radio opaque material is disposed on the outer surface of the member in the vicinity of the distal end of the same. A tubular member of a plastic material is carried by the distal end of the elongate member and encapsulates the metallic band to prevent the same from becoming dislodged from the distal end of the catheter.

The catheter tip marker of the present invention can be applied to various types of catheters. For example, balloon-type catheters of the type disclosed in U.S. Pat. No. 4,323,071 can be utilized. In addition balloon-type catheters of the type disclosed in co-pending application Ser. No. 522,835 filed 8-12-83 can be utilized. The balloon catheter 11 shown in FIG. 1, for example, can be one of the type disclosed in U.S. Pat. No. 4,323,071. It consists of an elongate flexible member 12 which is provided with a cylindrical outer surface 13 and with a proximal end (not shown) and a distal end 16. In the embodiment of the invention shown in FIG. 1, the elongate flexible member 12 is formed of a plastic tubular member which is provided with a central lumen or flow passage 17. A marker in the form of a circular band 21 is disposed on the distal end of the member 12 and engages the outer cylindrical surface 13. The band 21 is formed of a suitable radio opaque material such as a gold alloy. Other radio opaque materials which can be utilized for this purpose are tungsten and platinum. By way of example, the ring or band 21 can be formed of a gold alloy. In one application the band had an inside diameter of 0.029 inches, a wall thickness of 0.002 inches and had a width of approximately 0.02 inches.

Means is provided for encapsulating the band 21 onto the distal end of the elongate member 12 and consists of an elongate flexible member 22 formed of a suitable material such as a heat shrinkable plastic. This elongate flexible member 22 can be slipped over the distal end 16 of the member 12 and over the band 21 and then heat fused onto opposite sides of the band to shrink the elongate flexible member 22 onto the elongate member 12 to encapsulate the band 21 so that it cannot accidentally become dislodged from the outer extremity or distal end of the elongate member 12.

In the embodiment of the invention shown in FIG. 1, the elongate flexible member 22 is only a portion of a elongate flexible tubular member which extends the length of the catheter and which provides a flow passage 24 extending axially of the member 12 and between the outer surface of the member 12 and the inner surface of the elongate flexible tubular member 23. Also a balloon 26 is formed in the elongate flexible member 22 and is positioned near the distal end of the member 12. The balloon 26, as shown, is formed integral with the flexible member 22 and provides a chamber 27 which surrounds or encircles the member 12. It should be appreciated that if desired, the balloon 26 can be formed of a separate plastic tubular member which can be bonded or sealed to the elongate flexible member 22. The chamber 27 formed by the balloon 26 is in communication with the flow passage 24 extending to the proximal end of the catheter 11. When the elongate flexible member 22 is provided with a balloon such as the balloon 26, the band can be encapsulated by heat fusing the plastic material at annular regions 28 and 29 on opposite sides of the band.

In order to facilitate this fusing of the plastic at the distal end of the catheter, a mandrel in the form of a cylindrical rod can be inserted into the distal end of the member 12 during the time that the fusing is taking place to ensure that a minimum sized opening is provided in the catheter 11 and to ensure that a good seal is formed between the elongate flexible member 22 and the outer surface of the member 22 on opposite sides of the band 21. In larger diameter catheters, it may be desirable to add a filler material 31 as shown in FIG. 1 between the band 21 and the distal end of the catheter to provide a smoother transition. The filler material 31 can be formed of a plastic similar to the plastic of members 12 and 22 to conform and fuse to the elongate flexible member 22. When heat fusion takes place, the filler material 31 will be shifted so that there is a smooth gradation from the extreme tip of the catheter up and over the band 21.

As shown by the catheter 36 in FIG. 2 which is representative of the smaller type catheters as, for example, having a balloon diameter of less than 2.5 mm, a construction similar to that shown in FIG. 1 can be used. Because of the small size of the catheter the filler material 31 can be eliminated and the elongate flexible member can be heat shrunk directly over the band 21 to encapsulate the same leaving at most a small annular void at 37.

Another catheter on which the tip marker of the present invention can be utilized is shown in FIG. 3. It is a reperfusion catheter. Typically such a catheter is utilized for infusion of enzymes such as streptokinase and urokinase directly at the site of an occlusion in a coronary artery. The enzyme, as is well known to those skilled in the art, dissolves the clot in the coronary artery and opens the coronary artery allowing reperfusion of the myocardium.

In order to make possible more accurate placement of the tip of such a reperfusion catheter, the tip marker of the present invention is particularly useful. The catheter 41 shown in FIG. 3 is a reperfusion cathether which has a tip marker of the present invention. The catheter 41 consists of a flexible elongate assembly 42 and a three arm fitting 43 which is secured to the flexible elongate assembly 42. The tip marker is positioned near the distal end of the elongate assembly 42 at 44 as shown in FIG. 3 and in FIG. 4.

The flexible elongate assembly 42 consists of a flexible elongate tubular member 46 formed of a suitable material such as a heat shrinkable plastic which is provided with a central lumen or flow passage 47. The tubular member 46 is provided with a proximal end at 48 and a distal end at 49. The distal end 49 is reduced in thickness by stretching the same under heat. A radio opaque band 51 of the type hereinbefore described is then seated on the outer extremity of the flexible member 46. This band 51 in a cross section extending axially of the band is generally rectangular. The band also has a planar outer cylindrical surface.

As soon as the band 51 has been positioned, an additional flexible elongate tubular member 52 of relatively short length is passed over the band 51 and the thinned out distal portion of the elongate member 46 as shown in FIG. 4. The tubular member 52 is formed of a suitable heat shrinkable plastic and is heat fused to cause the same to shrink downwardly over the band 51 and also to firmly encapsulate the band by shrinking down at regions 53 and 54 on opposite sides of the band. In order to maintain a minimum sized flow passage at the distal extremity at the elongate flexible member 46, a mandrel in the form of a cylindrical rod (not shown) can be inserted into the flow passage 47 prior to the application of heat to the tubular member 52. This ensures that an opening of the desired size is maintained. It also ensures that the plastic will be heat fused to shrink tightly onto the distal end of the catheter. Only a small annular void remains as shown at 56 in FIG. 4. As can be seen, a relatively smooth transition occurs as the tubular member 52 extends over the band 51 and encapsulates the same. The flexible elongate member 46 is secured to the fitting 43 in a conventional member such as, for example, by the use of two heat shrinkable plastic sleeves 57 and 58.

To use the reperfusion catheter 41 shown in FIGS. 3 and 4, the catheter is inserted into the coronary artery by the use of a guide wire 61 extending through the central arm 62 of the fitting 43. The catheter is advanced over the guide wire 61 until the gold band which is being viewed under a fluoroscope reaches the desired occlusion in the coronary artery. After the catheter has been properly positioned, the guide wire 61 can be removed. The two side arms 63 and 64 of the fitting 43 are each provided with a valve assembly 66 of the type disclosed in co-pending application Ser. No. 343,435 filed Jan. 28, 1982. These valve assemblies serve as check valves to prevent outflow from the side arms. These side arms 63 and 64 can be utilized for introduction of a radio opaque medium or for the dripping of an enzyme into the coronary artery as is well known to those skilled in the art.

It is apparent that there has been provided in the present invention a tip marker which is particularly applicable to various types of catheters. The tip marker of the present invention has been totally encapsulated so as to prevent any accidental dislodgement of the tip marker from the distal end of the catheter. This is true even though the catheter is of a very small diameter.

What is claimed is:

1. In a catheter, a first elongate flexible member having a cylindrical outer surface and having proximal and distal ends, a metallic band of radio opaque material disposed on the outer surface of the elongate member in the vicinity of the distal end of the elongate member, a tubular member of a flexible material carried by the distal end of the elongate member and encapsulating the metallic band to prevent its accidental dislodgment from the tip of the catheter the tubular member having formed therein, at the distal end thereof, an annular recess which receives the metallic band.

2. A catheter as in claim 1 wherein the flexible elongate member is provided with a central lumen.

3. A catheter as in claim 1 wherein the tubular member extends the length of the catheter, together with a balloon formed on the distal end of the elongate member and providing a chamber and wherein the tubular member in conjunction with the elongate flexible member provides a flow passage extending into the chamber.

4. A catheter as in claim 1 wherein the catheter is a balloon-type catheter.

5. A catheter as in claim 1 wherein the catheter is a reperfusion-type catheter.

6. A catheter as in claim 1 in which the band in a cross section extending axially of the band is generally rectangular.

7. A catheter as in claim 1 in which the band has a planar outer cylindrical surface.

* * * * *